United States Patent [19]
Tsukamoto et al.

[11] Patent Number: 5,843,428
[45] Date of Patent: Dec. 1, 1998

[54] DISEASE-CONTROLLING AGENT AND DISEASE CONTROL METHOD FOR USEFUL GRAMINEOUS PLANTS

[75] Inventors: Hiroshi Tsukamoto; Yoko Fukuhara; Fumiki Tsutsumi; Masao Yamada, all of Yokohama; Tsuneo Namai, Tsuruoka, all of Japan

[73] Assignee: Japan Tobacco Inc., Tokyo, Japan

[21] Appl. No.: 507,480

[22] PCT Filed: Dec. 28, 1994

[86] PCT No.: PCT/JP94/02286

§ 371 Date: Aug. 28, 1995

§ 102(e) Date: Aug. 28, 1995

[87] PCT Pub. No.: WO95/17820

PCT Pub. Date: Jul. 6, 1995

[30] Foreign Application Priority Data

Dec. 28, 1993 [JP] Japan ................................. 5-337906

[51] Int. Cl.⁶ .................................................. A01N 13/00
[52] U.S. Cl. ...................... 424/93.5; 435/254.1; 435/911
[58] Field of Search ...................... 424/93.5; 435/254.1, 435/911

[56] References Cited

U.S. PATENT DOCUMENTS

| | | | |
|---|---|---|---|
| 3,661,935 | 5/1972 | Aldridge et al. | 260/343.2 R |
| 4,808,207 | 2/1989 | Gotlieb et al. | 71/73 |
| 5,332,573 | 7/1994 | Yamaguchi et al. | 504/117 |
| 5,424,271 | 6/1995 | Yamaguchi et al. | 504/117 |
| 5,498,592 | 3/1996 | Gohbara et al. | 504/117 |
| 5,530,146 | 6/1996 | Arai et al. | 549/476 |

FOREIGN PATENT DOCUMENTS

| | | |
|---|---|---|
| 0605221 | 7/1994 | European Pat. Off. . |
| 2-35076 | 2/1990 | Japan . |
| 3-219883 | 9/1991 | Japan . |
| 4-360678 | 12/1992 | Japan . |
| 4-370090 | 12/1992 | Japan . |
| 5-65209 | 3/1993 | Japan . |
| 6-277042 | 10/1994 | Japan . |

OTHER PUBLICATIONS

ATCC Catalogue of Filamentous Fungi, 18th ed., pp. 159, 172, 173, 208, and 383, 1991.
Mori, K. et al., Tetrahedron, vol. 45(6), pp. 1639–1646, 1989.
Robeson, D.J. et al., Agric. Biol. Chem., vol. 46(11), pp. 2681–2683, 1982.
Leonard & Suggs, Mycologia, vol. 66, pp. 290–297, 1974.
Alcorn, J.L., Mycotaxon, vol. 7(2), pp. 411–414, Jul. 1978.
Lenne, J.M. et al., Plant Disease, vol. 74(12), pp. 945–951, Dec. 1990.
Leonard, K.J. et al., Plant Disease, vol. 72(12), pp. 1034–1038, Dec. 1988.
M. Iwano "Bull. Tohoku Natl. Agric Exp. STN" 75, pp. 27–39 (1987).
Y. Fujita et al "Ann. Phytopath. Soc" Japan 56, 1990, pp. 273–275 Apr. #2.
Gnanamanickam. S.S. et al. "Ann. Phytopath Soc." Japan 58, 1992—pp. 380–385 Jun. #3.
"Mycological Papers" No. 158, Issued Nov. 10, 1987—pp. 211–212 Sivanesan, A.
J. L. Alcorn "Mycotaxon" vol. VII, No. 2, pp. 411–414—Jul.–Sep. 1978.
E.S. Luttrell "Pyrenophora, Cochliobolus & Setosphaeria" pp. 271–279 #7—Revue de Mycologie vol. 41, 1977.
M.B. Ellis "Dematiaceous Hyphomycetes"—pp. 402–453 (AB Int. 1971.

*Primary Examiner*—Irene Marx
*Attorney, Agent, or Firm*—Birch, Stewart, Kolasch & Birch, LLP

[57] ABSTRACT

The present invention relates to a disease-controlling agent for useful gramineous plants such as rices, corns, wheats, barleys, ryes and oats, comprising as an active ingredient a microorganism belonging to the genus Exserohilum and having an ability to control diseases of useful gramineous plants, as well as a disease control method for gramineous plants comprising applying said agent to useful gramineous plants including rices, corns, wheats, barleys, ryes and oats.

1 Claim, No Drawings

DISEASE-CONTROLLING AGENT AND DISEASE CONTROL METHOD FOR USEFUL GRAMINEOUS PLANTS

TECHNICAL FIELD

The present invention relates to a disease-controlling agent and a disease control method for useful gramineous plants using a microorganism belonging to the genus Exserohilum.

BACKGROUND ART

In the culturing of rice, blast is the most commonly occurring disease, causing decreases in yield. Therefore, the application of a fungicide is required from once to 3–4 times annually.

However, in view of the problem of environmental pollution caused by chemical pesticides recently, the development of an agent for controlling crop diseases which does not depend on a chemical pesticide as well as a method for using the agent has been desired.

Because of this need disease control methods using microorganisms have been developed. These methods can be classified into two groups, depending on the means employed. One is a method where a *Pyricularia oryzae* (pathogen causing rice blast) which exhibits incompatibility for a certain rice variety is inoculated into the rice variety to thereby induce its resistance against diseases and control rice blast. Examples of this method include one described in Bull. Tohoku Natl. Agric. Exp. Stn. 75, 27–39 (1987) and one described in Annals of the Phytopathological Society of Japan, Vol. 56, No. 2, pp. 273–275 (1990). In addition, there is a similar method where a rice variety is inoculated with a microorganism isolated from rice which exhihibits weak pathogenicity against rice to thereby induce its resistance against diseases and control rice blast. This method is described, for example, in Annual Report of the Society of Plant Protection of North Japan, No. 30, pp. 53–55 (1979).

The second method is one where a microorganism which exhibits antagonism against *Pyricularia oryzae* (pathogen causing rice blast) is used to control rice blast. Examples of this method include one described in Annals of the Phytopathological Society of Japan, Vol. 58, No.3, pp. 380–385 (1992) and those described in Japanese Unexamined Patent Publications Nos. 2-35076 and 5-65209.

PROBLEM FOR SOLUTION BY THE INVENTION

However, the above-mentioned method where a *Pyricularia oryzae* incompatible race is used to induce resistance against diseases has the following problem. That is, since the property of "incompatibility" is a relative property between a certain race of the pathogen and a certain variety of the target crop, a race exhibiting incompatibility for one variety can exhibit compatibility for other varieties. Therefore, the application of a *Pyricularia oryzae* itself over a rice growing field involves a risk of causing rice blast in varieties of rice which exhibit compatibility for the applied *Pyricularia oryzae*. In particular, in such an area where a number of different varieties are grown, the possibility of causing rice blast increases if there is a rice variety with compatibility grown. Furthermore, incompatible races may be mutagenized into compatible races. Thus, there is the danger of such compatible races being mixed into the incompatible races to be applied.

In another method mentioned above where a microorganism isolated from rice is inoculated to induce resistance against diseases, *Helminthosporium oryzae* (*Bipolaris oryzae*) exhibits extremely high control effects against blast. However, since this microorganism is the pathogen causing rice Helminthosporium leaf spot, it is not applicable to a rice growing field.

The above-mentioned method of using a microorganism exhibiting antagonism against *Pyricularia oryzae* generally produces low control effects in many cases. For example, according to the method described in Annals of the Phytopathological Society of Japan, Vol. 58, No.3 supra, control effects against blast is only about 50%. In addition, microorganisms used in this method are pathogens of useful plants in many cases, and thus there is a risk of causing adverse effects on other useful plants. For example, the method described in Japanese Unexamined Patent Publication No. 2-35076 uses the pathogen causing gladiolus bacterial soft rot and the method described in Japanese Unexamined Patent Publication No. 5-65209 uses the pathogen (*Gibberella fujikuroi*) causing rice "Bakanae" disease.

For the above-mentioned reasons, disease control methods using microorganisms are little utilized at present despite the strong social demand.

Under such circumstances, it is the object of the present invention to provide a means for controlling crop diseases, such as blast, without causing adverse effects on the growth of useful plants such as rices.

DISCLOSURE OF THE INVENTION

The present inventors have made intensive and extensive studies on weed pathogens which do not cause adverse effects on the growth of useful plants. As a result, it was found that strains belonging to the genus Exserohilum spp. which is a pathogen of barnyard grass exhibit high control effects against diseases of useful gramineous plants. Hereinafter the term "useful gramineous plants" is intended to include varieties of rice, corn, wheat, barley, rye and oat. Thus, the present invention has been accomplished.

In one aspect of the present invention, there is provided a disease-controlling agent for useful gramineous plant, comprising as an active ingredient a microorganism belonging to the genus Exserohilum and having an ability to control diseases of useful gramineous plants. With respect to the microorganism belonging to the genus Exserohilum, *Exserohilum monoceras* may be used. Examples of preferable strains include *Exserohilum monoceras* B026, *Exserohilum monoceras* B276, *Exserohilum monoceras* B232, *Exserohilum monoceras* B263, *Exserohilum monoceras* B267, *Exserohilum monoceras* JTB-159, *Exserohilum monoceras* JTB-215, *Exserohilum monoceras* JTB-240, *Exserohilum monoceras* JTB-264, *Exserohilum monoceras* JTB-277, *Exserohilum monoceras* JTB-281, *Exserohilum monoceras* JTB-673, *Exserohilum monoceras* JTB-674, *Exserohilum monoceras* JTB-675, *Exserohilum monoceras* JTB-676, *Exserohilum monoceras* JTB-677, *Exserohilum monoceras* JTB-678, *Exserohilum monoceras* JTB-679 and *Exserohilum monoceras* JTB-680.

In another aspect of the present invention, there is provided a disease control method for useful gramineous plants, comprising applying to useful gramineous plants a microorganism belonging to the genus Exserohilum and having an ability to control diseases of useful gramineous plants.

In a further aspect of the present invention, there is provided a strain selected from the group consisting of *Exserohilum monoceras* B026, *Exserohilum monoceras* B276, *Exserohilum monoceras* B232, *Exserohilum monoceras* B263, *Exserohilum monoceras* B267, *Exserohilum* monoceras JTB-159, *Exserohilum monoceras* JTB-215, *Exserohilum monoceras* JTB-240, *Exserohilum monoceras* JTB-264, *Exserohilum monoceras* JTB-277, *Exserohilum monoceras* JTB-281, *Exserohilum monoceras* JTB-673, *Exserohilum monoceras* JTB-674, *Exserohilum monoceras* JTB-675, *Exserohilum monoceras* JTB-676, *Exserohilum monoceras* JTB-677, *Exserohilum monoceras* JTB-678, *Exserohilum monoceras* JTB-679 and *Exserohilum monoceras* JTB-680.

Hereinbelow, the present invention will be described in more detail.

With respect to the microorganism to be used for the present invention, there is no particular restriction as long as the microorganism belongs to the genus Exserohilum. Preferably, a microorganism belonging to *Exserohilum monoceras* is used. As preferable strains, *Exserohilum monoceras* B026, *Exserohilum monoceras* B276, *Exserohilum monoceras* B232, *Exserohilum monoceras* B263, *Exserohilum monoceras* B276, *Exserohilum monoceras* JTB-159, *Exserohilum monoceras* JTB-215, *Exserohilum monoceras* JTB-240, *Exserohilum monoceras* JTB-264, *Exserohilum monoceras* JTB-277, *Exserohilum monoceras* JTB-281, *Exserohilum monoceras* JTB-673, *Exserohilum monoceras* JTB-674, *Exserohilum monoceras* JTB-675, *Exserohilum monoceras* JTB-676, *Exserohilum monoceras* JTB-677, *Exserohilum monoceras* JTB-678, *Exserohilum monoceras* JTB-679, *Exserohilum monoceras* JTB-680 and the like may be enumerated.

The above-mentioned strains have been deposited under the terms of the Budapest Treaty in the National Institute of Bioscience and Human-Technology, Agency of Industrial Science and Technology 1–3, Higashi 1-chome, Tsukuba-shi, Ibarkari-ken, 305, Japan under the following accession numbers.

*Exserohilum monoceras* B026: FERM BP-4215

(Original deposit date: Mar. 5, 1993)

*Exserohilum monoceras* B276: FERM BP-4220

(Original deposit date: Mar. 5, 1993)

*Exserohilum monoceras* B232: FERM BP-4217

(Original deposit date: Mar. 5, 1993)

*Exserohilum monoceras* B263: FERM BP-4218

(Original deposit date: Mar. 5, 1993)

*Exserohilum monoceras* B267: FERM BP-4219

(Original deposit date: Mar. 5, 1993)

*Exserohilum monoceras* JTB-159: FERM BP-4812

(Original deposit date: Oct. 3, 1994)

*Exserohilum monoceras* JTB-215: FERM BP-4813

(Original deposit date: Oct. 3, 1994)

*Exserohilum monoceras* JTB-240: FERM BP-4814

(Original deposit date: Oct. 3, 1994)

*Exserohilum monoceras* JTB-264: FERM BP-4815

(Original deposit date: Oct. 3, 1994)

*Exserohilum monoceras* JTB-277: FERM BP-4816

(Original deposit date: Oct. 3, 1994)

*Exserohilum monoceras* JTB-281: FERM BP-4817

(Original deposit date: Oct. 3, 1994)

*Exserohilum monoceras* JTB-673: FERM BP-4915

(Original deposit date: Dec. 8, 1994)

*Exserohilum monoceras* JTB-674: FERM BP-4916

(Original deposit date: Dec. 8, 1994)

*Exserohilum monoceras* JTB-675: FERM BP-4917

(Original deposit date: Dec. 8, 1994)

*Exserohilum monoceras* JTB-676: FERM BP-4918

(Original deposit date: Dec. 8, 1994)

*Exserohilum monoceras* JTB-677: FERM BP-4919

(Original deposit date: Dec. 8, 1994)

*Exserohilum monoceras* JTB-678: FERM BP-4920

(Original deposit date: Dec. 8, 1994)

*Exserohilum monoceras* JTB-679: FERM BP-4921

(Original deposit date: Dec. 8, 1994)

*Exserohilum monoceras* JTB-680: FERM BP-4922

(Original deposit date: Dec. 8, 1994)

These strains have been isolated from diseased weed (barnyard grass) and have the following fungalogical properties.

They are aerobic and their colonies on a potato sucrose agar medium reveal a deep, dark green color or black color. Occasionally, white or grey air hyphae are observed. Their conidia are dark-colored and multipored with about 2 to 8 septa. They are spindle-shaped, shaped, being widest at the central portion and becoming thinner toward the ends. A hilum is protruding from the bottom end of these conidia. The size of conidium is about $40-150 \times 10-25$ $\mu$m.

By checking the above results with two document s of A. Sivanesan, "Graminicolous Species of Bipolaris, Curvularia, Drechslera, Exserohilum and Their Teleomorphs", Mycological Pagers, No. 158, p. 211, Nov. 1987 and Ueda, Tsuda and Nishiyama, "Scientific Names for the So-Called Helminthosporium Pathogen Family", Plant Protection, Vol. 32, No. 9, pp. 361–368, 1978, the above-mentioned strains have been identified as an *Exserohilum monoceras* mainly because the shape of their colonies and the morphology of their conidia were identical with those of *Exserohilum monoceras*.

The name "genus Exserohilum" has been employed according to the classifications made by Ueda, Tsuda and Nishiyama and A. Sivanesan mentioned above. Luttrell [Revue de Mycologie, Vol. 41, pp. 271–279, (1977)] and Alcorn (Mycotaxon, Vol. 8, pp. 411–414, 1978) also supports this classification. On the other hand, Ellis

[Dematioceous Hyphomycetes, CMI, Kew, 608 (1971)] includes both the genus Exserohilum and the genus Bipolaris in the genus Drechslera, employing only the last one. However, except Ellis, recently there have been no researchers who do not recognize the genus Exserohilum and the genus Bipolaris. Therefore, it seems appropriate to employ the "genus Exserohilum". In addition, since it is known that the teleomorph of the genus Exserohilum is the genus Setosphaeria, those microorganisms classified into the genus Setosphaeria are also included in the scope of the present invention.

The culturing of the above-mentioned Exserohilum strains does not require special methods; methods similar to those used for culturing known Exserohilum strains may be used. With respect to the medium, either synthetic media or natural media may be used as long as they contain an assimilable carbon source, a nitrogen source, minerals, and necessary growth promoting substances appropriately. Concrete examples of such media include oatmeal sucrose agar medium, oatmeal agar medium, potato sucrose agar medium, V-8 juice agar medium, Czapek-Dox agar medium and the like. In the culturing, it is desirable to keep the temperature at 10° to 40° C., preferably 15° to 28° C., and more preferably 20° to 25° C. while keeping the pH at 3 to 9, preferably 5 to 8. When the strains have grown under these conditions for about 7 to 14 days, a sufficient amount of conidia is formed on the surface of the medium.

When the strain of the present invention is used in the disease control method, cells (such as conidia, ascospores, hyphae, etc.) of the microorganism are used; preferably, the conidia produced by the strain are used. Conidia can be harvested by pouring sterile water over the colonies and scratching off the surface of the medium with a writing brush. According to these procedures, $1 \times 10^7$ to $10^8$ conidia can be obtained per one laboratory dish 9 cm in diameter.

As the disease-controlling agent of the present invention, the microorganism may be used as it is; generally, however, the microorganism is mixed with a solid or liquid carrier acceptable for pesticides, formulated and used in the form of a liquid formulation, wettable powder, granule, emulsifiable concentrate, oil solution, capsule, and the like.

As the microorganism, usually conidia thereof are used. The suitable concentration of conidia in the case of a liquid formulation is $10^3$ to $10^7$ conidia/ml, preferably $10^4$ to $10^6$ conidia/ml.

When the microorganism is actually applied to a field, it is desirable to adjust the amount of application so that the number of its conidia becomes $10^8$ to $10^{12}$ preferably $10^9$ to $10^{11}$ per 10 ares of the field.

The target diseases to be controlled according to the present invention include rice blast, rice Helminthosporium leaf spot, rice bacterial leaf blight, rice sheath blight, corn leaf spot, corn smut, corn leaf blight, and various kinds of smut of wheat, barley, rye and oat.

BEST MODE FOR CARRYING OUT THE INVENTION (EXAMPLE 1)

Selection of Strains such as B026, B232, B263, B267 and B276

Diseased weeds were collected from all over Japan and fungal pathogens were isolated from lesions. The control effects of these pathogens against rice blast were investigated according to the method mentioned below.

The weed pathogen was applied to healthy rice plants (variety: Koshihikari). After the plants had been kept in a greenhouse for an arbitrary period of time, a *Pyricularia oryzae* which exhibits compatibility for this rice variety was inoculated thereinto. About one month from the inoculation, disease indices of rice blast were evaluated comprehensively and the barnyard grass pathogens (strains of B026, B232, B263, B267, B276, JTB-159, JTB-215, JTB-240, JTB-264, JTB-277, JTB-281, JTB-673, JTB-674, JTB-675, JTB-676, JTB-667, JTB-678, JTB-679 and JTB-680) which exhibited the highest effects was selected.

(EXAMPLE 2)

Control Effects of the 19 Strains of Barnyard Grass Pathogen against Rice Blast

Seeds of rice (variety: Koshihikari) were sown in 1/10000 are pots and grown in a greenhouse for about 4 weeks. Then, 1% aqueous ammonium sulfate solution was supplied as a fertilizer. The resultant plants were kept in a greenhouse further for about one week, and then the plants at 6-leaf stage were used for testing the control effects.

The 19 strains of the barnyard grass pathogen were individually grown on an oatmeal sucrose agar medium for 2 weeks at 25° C. for the formation of conidia. These conidia were suspended in 0.02% Tween 20 aqueous solution, and then the concentration was adjusted to $10^5$ or $10^6$ conidia/ml, to thereby obtain treating solutions of different concentrations. Each of these conidium suspensions was sprayed over the plants at a rate of 1 ml/pot with a sprayer, and then the plants were placed in a dew chamber kept at 25° C. under 100% humidity for 20 hours. Three pots were treated for each test plot.

After these pots had been kept in a greenhouse for 2 days, a suspension of conidia ($10^5$ conidia/ml 0.02% Tween 20 aqueous solution) from *Pyricularia oryzae* race 007 which exhibits compatibility for the rice variety Koshihikari was spray-inoculated into the plants at a rate of 1 ml/pot, and then the plants were placed in a dew chamber kept at 25° C. under 100% humidity for 20 hours.

One week after the inoculation, the average number of lesions per sixth leaf was investigated and the percent control was calculated by the formula mentioned below.

TABLE 1

Control Effects of the Barnyard Grass Pathogen against Rice Blast

| | Percent Control against Rice Blast Conidium Concentration of Barnyard Grass Pathogen | |
|---|---|---|
| | $10^6$ conidia/ml | $10^5$ conidia/ml |
| No treatment | − | − |
| B026 | +++ | ++ |
| B232 | +++ | +++ |
| B263 | +++ | ++ |
| B267 | +++ | ++ |
| B276 | +++ | +++ |
| JTB-159 | +++ | +++ |
| JTB-215 | +++ | +++ |
| JTB-240 | +++ | + |
| JTB-264 | +++ | ++ |

TABLE 1-continued

Control Effects of the Barnyard Grass Pathogen
against Rice Blast

| | Percent Control against Rice Blast Conidium Concentration of Barnyard Grass Pathogen | |
|---|---|---|
| | $10^6$ conidia/ml | $10^5$ conidia/ml |
| JTB-277 | +++ | +++ |
| JTB-281 | +++ | +++ |
| JTB-673 | +++ | +++ |
| JTB-674 | +++ | +++ |
| JTB-675 | +++ | +++ |
| JTB-676 | +++ | +++ |
| JTB-677 | +++ | +++ |
| JTB-678 | +++ | +++ |
| JTB-679 | +++ | +++ |
| JTB-680 | +++ | +++ |

Percent Control = (1 - Average Number of Lesions in Treated Plot/Average Number of Lesions in Non-treated Plot) × 100
Ratings of Percent Control:
0–25%: –
26–50%: +
51–75%: ++
76–100%: +++

As shown in Table 1, it was observed that any of the tested strains have high control effects against rice blast.

(EXAMPLE 3)

Persistency of the Control Effects against Rice Blast

Seeds of rice (variety: Koshihikari) were sown in 1/10000 are pots and grown in a greenhouse for about 3 weeks. Then, 1% aqueous ammonium sulfate solution was supplied as a fertilizer. The resultant plants were kept in a greenhouse further for about one week, and then the plants at 4- to 5-leaf stage were used for testing the control effects.

The B026 strain of the barnyard grass pathogen was grown on an oatmeal sucrose agar medium for 2 weeks for the formation of conidia. These conidia were suspended in sterile water containing 0.02% Tween 80 and then the concentration was adjusted to $10^5$ or $10^6$ conidia/ml, to thereby obtain treating solutions of different concentrations. Each of these conidium suspensions was sprayed over the plants at a rate of 2 ml/pot with a sprayer, and then the plants were placed in a dew chamber kept at 25° C. under 100% humidity for 18 hours. Two pots were treated for each test plot.

After these pots had been kept in a greenhouse for 2, 3 or 9 days, a suspension of conidia ($10^5$ conidia/ml 0.02% Tween 80 aqueous solution) from *Pyricularia oryzae* race 013 which exhibits compatibility for the rice variety Koshihikari was spray-inoculated into the plants at a rate of 1 ml/pot, and then the plants were placed in a dew chamber kept at 25° C. under 100% humidity for 18 hours.

One week after the inoculation, the disease indices of rice blast were evaluated comprehensively (ratings: 0 for healthy plant; 100 for completely wilted and killed; the degree of growth of the plants, the number of blast lesions, etc. were taken into consideration). The percent control was calculated by the formula mentioned below.

TABLE 2

Days after Treatment with B026 and Control Effects
against Rice Blast

| | Percent Control No. of Days after the Treatment with Barnyard Grass Pathogen | | |
|---|---|---|---|
| Conidium Concentration (conidia/ml) | 2 | 3 | 9 |
| $10^5$ | 68 | 63 | 79 |
| $10^6$ | 74 | 74 | 79 |

Percent Control = (1 - Disease Index of Treated Plot/Disease Index of Non-treated Plot) × 100

As shown in Table 2, high control effects against rice blast were observed in any of the test plots treated at each of the concentrations, regardless of the period passed since the treatment with the barnyard grass pathogen.

(EXAMPLE 4)

Control Effects against Rice Blast by Treatment using a Seedling-Raising Box

Seeds of rice (variety: Koshihikari) were sown in a seedling-raising box (12×12×3 cm) and grown in an greenhouse. The resultant rice plants at 2- to 3-leaf stage were used for testing the control effects. A suspension of conidia from the strain JTB-277 ($10^5$ or $10^6$ conidia/ml 0.02% Tween 20 aqueous solution) was sprayed over the rice plants, which were then placed for 20 hours in a dew chamber kept at 25° C. under 100% humidity. After the plants had been kept in a greenhouse for 7 days, each 5 seedlings of them were transplanted to a 1/10000 are pot which had been given paddy field conditions by filling paddy field soil therein.

Fourteen days after the transplantation, the plants which had reached around 5-leaf stage were inoculated with *Pyricularia oryzae* race 007 which has compatibility for the variety Koshihikari. Then, the plants were placed in a dew chamber kept at 25° C. under 100% humidity for 18 hours. Seven days after the inoculation, the average number of lesions per fifth leaf was investigated and the percent control was calculated by the formula mentioned below. As a result, high control effects against rice blast were obtained as shown in Table 3 by treatment with the disease-controlling agent of the present invention using a seedling-raising box.

Percent Control =
(1 - Average Number of Lesions in Treated Plot/
Average Number of Lesions in Non-treated Plot) × 100

TABLE 3

| Conidium Concentration (conidia/ml) | Percent Control |
|---|---|
| 0 | 0 |
| $10^5$ | 78 |
| $10^6$ | 90 |

(Example 5) Control Effects against Rice Blast by Foliar Application (EXAMPLE 5)

Control Effects against Rice Blast by Foliar Application

In a field where rice seedlings (variety: Koshihikari) had been mechanically transplanted, triplicate of 4 test plots (Plots I–IV) totalling 12 were arranged, each plot being 4 m². Culture management was carried out conventionally. A suspension of the JTB-678 strain microorganism at a concentration of $10^6$ conidia/ml 0.02% Tween 20 aqueous solution was sprayed over the rice plants with a small size pressure sprayer at a rate of 100 liters/10 ares once for Plot I, twice for Plot II, three times for Plot III and four times for Plot IV.

After the flag leaf had been completely developed, 24 plants from each test plot were examined for the ratio of the area developing leaf blast, and the percent control against leaf blast was calculated by the formula given below. Further, 2 weeks prior to the harvest, 8 plant from each test plot were examined for the incidence of ear blast by severity, and the percent control against ear blast was calculated by the formula below which is generally used. As a result, by the foliar application of the disease-controlling agent of the present invention, high control effects against leaf blast and panicle blast as shown in Table 4 were obtained.

Percent Control against Leaf Blast =

(1 − Ratio of Diseased Area in Treated Plot/

Ratio of Diseased Area in Non-treated Plot) × 100

Percent Control against Panicle Blast =

(1 − Severity of Incidence* in Treated Plot/

Severity of Incidence* in Non-treated Plot) × 100

*Severity of Incidence of Panicle Blast =

$$\frac{(4A + 3B + 2C + D)}{4 \times \text{Total Number of Panicle Investigated}} \times 100$$

wherein
A: No. of panicles developing blast at the neck
B: No. of panicles developing blast in more than ⅔ rachis branches
C: No. of panicles developing blast in ⅓ to ⅔ rachis branches
D: No. of panicles developing blast in more than ⅓ rachis branches

TABLE 4

| Test Plot* | No. of Times of Treatment | Percent Control Leaf Blast | Panicle Blast |
| --- | --- | --- | --- |
| I | 1 | 100 | 88 |
| II | 2 | 100 | 91 |
| III | 3 | 100 | 93 |
| IV | 4 | 100 | 95 |

*Test Plot I: plants at 5- to 7-leaf stage were treated.
Test Plot II: plants at 5- to 7-leaf stage and 8- to 9-leaf stage were treated.
Test Plot III: plants at 5- to 7-leaf stage, 8- to 9-leaf stage and 10- to 11-leaf stage were treated.
Test Plot IV: plants at 5- to 7-leaf stage, 8- to 9-leaf stage, 10- to 11-leaf stage and 11- to 12-leaf stage were treated.

(EXAMPLE 6)

Control Effects against Rice Blast by Panicle Application

In a field where rice seedlings (variety: Koshihikari) had been mechanically transplanted, triplicate of 4 test plots totalling 12 were arranged, each plot being 4 m². Culture management was carried out conventionally. A suspension of the JTB-159 strain microorganism at a concentration of $10^6$ conidia/ml was sprayed once over the panicles of the rice plants with a small size pressure sprayer at a rate of 100 liters/10 ares. In the same manner as in Example 5, 2 weeks prior to the harvest, 8 plant from each test plot were examined for the incidence of panicle blast by severity, and the incidence of severity was calculated. The percent control against panicle blast was calculated by the formula described in Example 5. As a result, by the panicle application of the disease-controlling agent of the present invention, high control effects against panicle blast as shown in Table 5 were obtained.

TABLE 5

| | Percent Control against Panicle Blast |
| --- | --- |
| Treatment with JTB-159 | 99 |

(EXAMPLE 7)

Control Effects against Rice Helminthosporium Leaf Spot

Seeds of rice (variety: Koshihikari) were sown in 1/10000 are pots and grown in a greenhouse. The resultant plants at 4- to 5-leaf stage were used for testing the control effects. A conidium suspension of the JTB-679 strain or JTB-680 strain at a concentration of $10^5$ or $10^6$ conidia/ml 0.02% Tween 20 aqueous solution was sprayed over the plants, which were then placed in a dew chamber kept at 25° C. under 100% humidity for 20 hours. After these plants had been kept in a greenhouse for 1 day, *Bipolaris oryzae* was spray-inoculated into the plants, which were again placed in a dew chamber kept at 25° C. under 100% humidity for 20 hours. Seven days after the inoculation, the average number of lesions per leaf was investigated and the percent control was calculated by the formula described in Example 4. As shown in Table 6, the disease-controlling agent of the present invention prevented the incidence of rice Helminthosporium leaf spot.

TABLE 6

| Strain | Conidium Concentration (conidia/ml) | Percent Control |
| --- | --- | --- |
| JTB-679 | $10^5$ | 90 |
|  | $10^6$ | 99 |
| JTB-680 | $10^5$ | 87 |
|  | $10^6$ | 96 |

Use Examples

Formulation Example 1 (Liquid Formulation)

Conidia of *Exserohilum monoceras* B026 strain ($2 \times 10^9$) and Tween 80 (4 g) were added to sterile water (20 liters) and mixed, to thereby prepare a liquid formulation. This liquid formulation was applied to a paddy field of 1 are where the incidence of rice blast was expected.

Formulation Example 2 (Wettable Powder)

Conidia (from the JTB-680 strain) were suspended in a mixture of maltose (9%), clay (1%) and water (90%) at a concentration of $10^7$ conidia/ml. After air drying, the dried product was mixed and crushed to thereby prepare a wettable powder.

Formulation Example 3 (Wettable Powder)

Conidia (from the B-263 strain) were suspended in a mixture of lactose (9%), zeolite (1%) and water (90%) at a concentration of $10^7$ conidia/ml. After air drying, the dried product was mixed and crushed to thereby prepare a wettable powder.

Formulation Example 4 (Wettable Powder)

Conidia (from the JTB-674 strain) were suspended in a mixture of diatomaceous earth (15%), kaolin (77%) and polyoxyethylene alkyl phenyl ether (8%) at a concentration of $10^7$ conidia/g. After air drying, the dried product was mixed and crushed to thereby prepare a wettable powder.

Formulation Example 5 (Wettable Powder)

Conidia (from the JTB-159 strain) were suspended in a mixture of diatomaceous earth (33%), carboxymethyl cellulose (0.33%) and water (66.67%) at a concentration of $10^7$ conidia/ml. After air drying, the dried product was mixed and crushed to thereby prepare a wettable powder.

Formulation Example 6 (Dust)

Conidia (from the B-276 strain) were mixed in a mixture of hydroxypropyl-β-cyclodextrin (14%), white carbon (12%) and clay (74%) at a concentration of $10^7$ conidia/g. After air drying, the dried product was crushed homogeneously to thereby prepare a dust.

Formulation Example 7 (Granule)

Conidia (from the JTB-281 strain) were added to a mixture of β-cyclodextrin (15%), starch (2%), bentonite (18%), calcium carbonate (36%) and water (29%) at a concentration of $10^7$ conidia/g and kneaded. The resultant mixture was granulated with a granulator and then dried, to thereby prepare a granule formulation.

Formulation Example 8 (Emulsifiable Concentrate)

Conidia (from the JTB-675 strain) were added to a mixture of ammonium polyoxyethylene nonyl phenyl ether phosphate (18%), polyoxyethylene nonyl phenyl ether (6%), triethyl phosphate (29%) and tributyl phosphate (47%) at a concentration of $10^7$ conidia/g and suspended homogeneously, to thereby parepare an emulsifiable concentrate.

Formulation Example 9 (Oil Solution)

$10^7$ conidia (from the JTB-277 strain) were suspended in 1 ml of a mixture composed of spindle oil (95%), castor oil (4%) and silicone oil (1%) to therby prepare an oil solution.

Formulation Example 10 (Dry Flowable)

$10^7$ conidia (from the JTB-215 strain) were suspended in 1 ml of a composition composed of sodium alkylbenzenesulfonate (12%) and polyethylene glycol ether (88%) to thereby prepare a dry flowable.

Formulation Example 11 (Capsule)

$10^7$ conidia (from the JTB-679 strain) were suspended in 1 ml of a mixture composed of sodium alginate (0.7%), kaolin (5%), glycerol (15%) and water (79.3%) and dropped into 0.2M calcium acetate solution, to thereby obtain a capsule-like product. This product was cut fine, sieved and air dried, to thereby prepare a capsule.

Formulation Example 12 (Capsule)

$10^7$ conidia (from the JTB-678 strain) were suspended in 1 ml of a mixture composed of sodium alginate (0.7%), diatomaceous earth (5%), glycerol (15%) and water (79.3%) and dropped into 0.2M calcium chloride solution, to thereby obtain a capsule-like product. This product was cut fine, sieved and air dried, to thereby prepare a capsule.

Effect of the Invention

The present invention provides a novel disease-controlling agent and a disease control method for useful gramineous plants. Since the disease-controlling agent and the method use a microorganism isolated from a weed, there is no need of apprehension about environmental pollution. In addition, unlike conventional microbial pesticides, the agent and the method of the invention do not cause adverse effects on useful plants. The disease-controlling agent of the present invention can control diseases of useful gramineous plants by treating these plants even once, and at the same time, the agent exhibits control effects against all of the diseases developing throughout growth stages of useful gramineous plants. Thus, the agent of the present invention is extremely useful from the industrial view point.

We claim:

1. A method of controlling rice blast disease comprising applying to a rice plant an effective amount of a microorganism belonging to the species *Exserohilum monoceras* to colonize the rice plant in order to control said disease.

* * * * *